United States Patent
Lantzsch et al.

[11] Patent Number: 6,136,975
[45] Date of Patent: Oct. 24, 2000

[54] METHOD FOR PRODUCING TRIFLUOROACETOACETIC ACID ANILIDES

[75] Inventors: Reinhard Lantzsch, Wuppertal; Karl Steinbeck, Burscheid, both of Germany; Ulrich Kämpfen, Brig, Switzerland

[73] Assignee: Bayer Aktiengesellschaft, Leverkusen, Germany

[21] Appl. No.: 09/319,644

[22] PCT Filed: Dec. 8, 1997

[86] PCT No.: PCT/EP97/06842

§ 371 Date: Jun. 9, 1999

§ 102(e) Date: Jun. 9, 1999

[87] PCT Pub. No.: WO98/27057

PCT Pub. Date: Jun. 25, 1998

[30] Foreign Application Priority Data

Dec. 19, 1996 [DE] Germany ............ 196 52 955

[51] Int. Cl.⁷ ............. C07D 239/02; C07C 255/00
[52] U.S. Cl. ............. 544/312; 558/44; 558/418
[58] Field of Search ............. 544/312; 558/414, 558/418

[56] References Cited

U.S. PATENT DOCUMENTS

| | | | |
|---|---|---|---|
| 5,127,935 | 7/1992 | Satow et al. | 504/243 |
| 5,593,945 | 1/1997 | Andree et al. | 504/243 |
| 5,681,794 | 10/1997 | Andree et al. | 504/243 |

FOREIGN PATENT DOCUMENTS 4218159  12/1993  Germany .

OTHER PUBLICATIONS

J. Heterocyc. Chem., Jun. 2, 1965, pp. 120–125, Dey et al, Synthesis and Properties of Fluorine–Containing Heterocyclic Compounds. II. Trifluoromethyl Benzo[h]quinolines, Benzo[h]–1,6–napthyridines, 1,7– and 1,10–Phenanthrolines (1).

*Primary Examiner*—Joseph K. McKane
*Assistant Examiner*—Joseph Murray
*Attorney, Agent, or Firm*—Joseph C. Gil

[57] ABSTRACT

By a novel process, trifluoroacetoacet-anilides of the formula

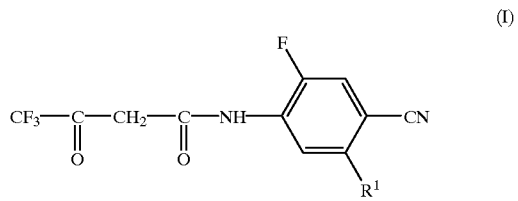

(I)

in which

R¹ is as defined in the description, can be prepared by reacting trifluoroacetoacetyl chloride with anilines of the formula

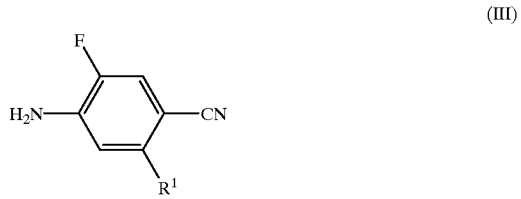

(III)

if appropriate in the presence of an acid binder and if appropriate in the presence of a diluent.

The compounds of the formula (I) are suitable intermediates for preparing herbicidally active uracil derivatives.

7 Claims, No Drawings

METHOD FOR PRODUCING TRIFLUOROACETOACETIC ACID ANILIDES

The instant Application is a 371 of PCT/EP97/06842 filed on Dec. 8, 1997.

TECHNICAL FIELD OF THE INVENTION

The present invention relates to a novel process for preparing trifluoroacetoacid-anilides which can be used as intermediates for preparing herbicidally active uracil derivatives.

BACKGROUND OF THE INVENTION

It is already known that N-aryl-trifluoroacetoacet-amides can be prepared by reacting trifluoroacetoacetic ester with aryl amines (cf. DE-A 42 18 159, EP-A 0 598 436 and J. Het. Chem. 2 (1965), 124). However, this process has the disadvantages that it is not widely applicable and that the desired products are only obtained in relatively low yields owing to interfering side reactions. Thus, to a considerable extent, the aryl amine attacks the carbonyl group which is adjacent to the trifluoromethyl group. The resulting enamine readily reacts with a further arylamine molecule, giving bis-adducts. This reaction can be illustrated by the following equation:

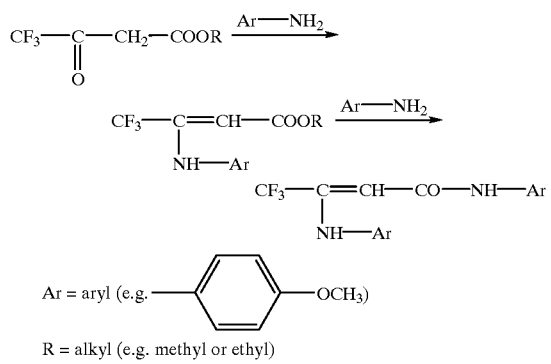

Furthermore, it is known that N-aryl-trifluoroacetoacet-amides can be prepared by eliminating one molecule of aryl amine from the bis-adducts of the abovementioned structure (cf. DE-A 42 18 159). It is a disadvantage of this process that it requires one step more than the method described above. Moreover, even here the yields are unsatisfactory for realizing the reaction on an industrial scale.

DETAILED DESCRIPTION OF THE INVENTION

It has now been found that trifluoroacetoacid-anilides of the formula

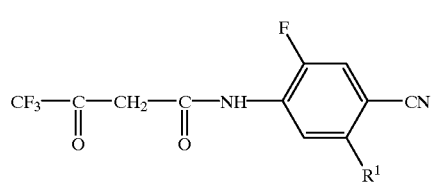

(I)

in which

R$^1$ represents halogen or a radical of the formula

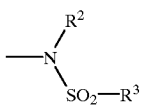

in which

R$^2$ represents hydrogen or optionally substituted alkyl and

R$^3$ represents optionally substituted alkyl, optionally substituted cycloalkyl or represents optionally substituted aryl, are obtained when trifluoroacetoacetyl chloride of the formula

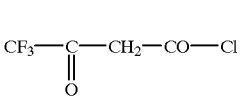

(II)

is reacted with anilines of the formula

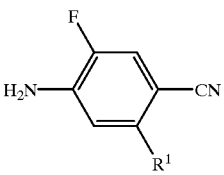

(III)

in which

R$^1$ is as defined above, if appropriate in the presence of an acid binder and if appropriate in the presence of a diluent, at temperatures between −20° C. and +40° C.

It is very surprising that trifluoroacetoacet-anilides of the formula (I) can be prepared by the process according to the invention in a smooth reaction with high yields. Such a reaction was unforeseeable, in particular because the trifluoroacetoacetyl chloride required as starting material is, even at low temperatures, only stable for a short period of time (cf. Chem. Abstr. 1964, 2788 f and GB-A 931 689). It is also surprising that those anilines of the formula (III) in which R$^1$ represents a radical of the formula —NH—SO$_2$—R$^3$ do not show any reaction worth mentioning of the trifluoroacetoacetyl chloride with the sulphonylamino group.

The process according to the invention has a number of advantages. Thus, the required starting materials are accessible in a simple manner and even in larger amounts. Furthermore, there are not any problems associated with the practice of the reaction and the isolation of the desired substances. It is particularly favourable that the trifluoroacetoacid-anilides are obtained in high yield and high purity. Furthermore, the process is widely applicable.

Using trifluoroacetoacetyl chloride and 4-cyano-2-fluoro-5-methylsulphonylamino-aniline as starting materials, the course of the process according to the invention can be illustrated by the following equation:

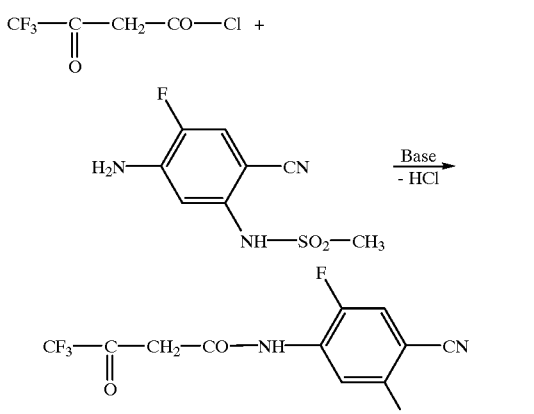

The trifluoroacetoacetyl chloride of the formula (II) required as starting material for carrying out the process according to the invention is known (cf. GB-A 931 689).

The formula (III) provides a general definition of the anilines furthermore required as starting materials for carrying out the process according to the invention. Preference is given to using compounds of the formula (III) in which $R^1$ represents fluorine, chlorine, bromine or a radical of the formula

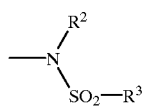

in which $R^2$ represents hydrogen or represents alkyl having 1 to 6 carbon atoms which is optionally substituted by cyano, halogen, alkoxy having 1 to 4 carbon atoms, alkylthio having 1 to 4 carbon atoms, alkylcarbonyl having 1 to 4 carbon atoms in the alkyl group or alkylaminocarbonyl having 1 to 4 carbon atoms in the alkyl moiety and $R^3$ represents alkyl having 1 to 6 carbon atoms, which is optionally substituted by cyano, halogen, $C_1$-$C_4$-alkoxy, $C_1$-$C_4$-alkylthio, $C_1$-$C_4$-alkylcarbonyl, $C_1$-$C_4$-alkoxycarbonyl, $C_1$-$C_4$-alkylaminocarbonyl or phenyl, or represents cycloalkyl having 3 to 6 carbon atoms which is optionally mono- to trisubstituted by identical or different substituents selected from the group consisting of halogen, cyano and alkyl having 1 to 4 carbon atoms, or represents phenyl which is optionally mono- to trisubstituted by identical or different substituents selected from the group consisting of halogen, cyano, alkyl having 1 to 4 carbon atoms, halogenoalkyl having 1 or 2 halogen atoms and 1 to 5 carbon atoms, alkoxy having 1 to 4 carbon atoms and halogenoalkoxy having 1 or 2 carbon atoms and 1 to 5 halogen atoms.

Particular preference is given to using anilines of the formula (III) in which $R^1$ represents fluorine, chlorine or a radical of the formula

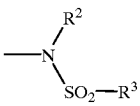

in which $R^2$ represents hydrogen or represents methyl, ethyl, n- or i-propyl, n-, i-, s- or t-butyl, each of which is optionally substituted by cyano, fluorine, chlorine, methoxy, ethoxy, methylthio, ethylthio, acetyl, propionyl, methoxycarbonyl, ethoxycarbonyl, methylaminocarbonyl or ethylaminocarbonyl and $R^3$ represents methyl, ethyl, n- or i-propyl, n-, i-, s- or t-butyl, each of which is optionally substituted by cyano, fluorine, chlorine, methoxy, ethoxy, methylthio, ethylthio, acetyl, propionyl, methoxycarbonyl, ethoxycarbonyl, methylaminocarbonyl, ethylaminocarbonyl or phenyl or represents cyclopentyl, cyclohexyl or cyclopropyl, which is optionally mono- to trisubstituted by identical or different substituents selected from the group consisting of fluorine, chlorine, cyano, methyl and ethyl, or represents phenyl which is optionally mono- to trisubstituted by identical or different substituents selected from the group consisting of fluorine, chlorine, cyano, methyl, ethyl, trifluoromethyl, methoxy, ethoxy, trifluoromethoxy and difluoromethoxy.

The anilines of the formula (III) are known or can be prepared by known methods (cf. EP-A 0 648 772).

Suitable acid acceptors for carrying out the process according to the invention are all customary inorganic or organic bases. Preference is given to using alkali metal or alkaline earth metal carbonates and bicarbonates, such as sodium carbonate, potassium carbonate or calcium carbonate, sodium bicarbonate, potassium bicarbonate or calcium bicarbonate, and also basic, organic nitrogen compounds, particular preference being given to trimethylamine, triethylamine, tripropylamine, tributylamine, ethyl-diisopropylamine, N,N-dimethyl-cyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl- piperidine, 1,4-diazabicyclo[2,2,2]-octane (DABCO), 1,5-diazabicyclo-[4,3,0]-non-5-ene (DBN), or 1,8 diazabicyclo [5,4,0]-undec-7-ene (DBU).

Suitable diluents for carrying out the process according to the invention are all customary inert, organic solvents. Preference is given to using aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; furthermore ethers, such as diethyl ether, diisopropyl ether, dioxane, tetrahydrofuran, ethyleneglycol dimethyl ether or ethylene glycol diethyl ether; tert-butyl methyl ether or tert-amyl-methyl ether, furthermore nitriles, such as acetonitrile, propionitrile or butyronitrile, and also esters, such as methyl acetate or ethyl acetate.

When carrying out the process according to the invention, the reaction temperatures can be varied within a certain range. In general, the process is carried out at temperatures between −20° C. and +40° C., preferably between −10° C. and +30° C.

The process according to the invention is generally carried out under atmospheric pressure. However, it is also possible to operate under elevated pressure.

The process according to the invention is preferably carried out under protective gas, such as nitrogen or argon.

When carrying out the process according to the invention, generally 1 to 3 mol, preferably 1 to 1.9 mol, of trifluoroacetoacetyl chloride of the formula (II) and 1 to 3 mol, preferably 1 to 1.9 mol of acid binder are employed per mole of aniline of the formula (III). In a preferred embodiment, the aniline of the formula (II) and the acid binder are initially charged in a diluent and trifluoroacetoacetyl chloride of the formula (II) is then added dropwise in a diluent. Work-up is carried out by customary methods. In general, the resulting crystalline product is filtered off, washed and dried. Any impurities that may still be present can be removed by customary methods (cf. Preparation Examples).

The trifluoroacetoacet-anilides of the formula (I) preparable according to the invention can be present in the "keto" form of the formula

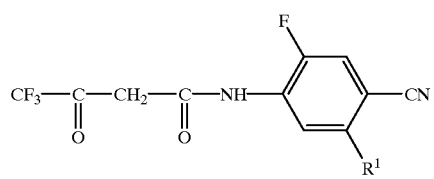

(I)

or as hydrate of the formula

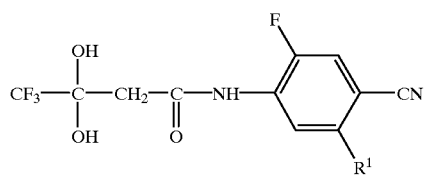

(Ia)

or in the "enol" form, which is tautomeric to (I), of the formula

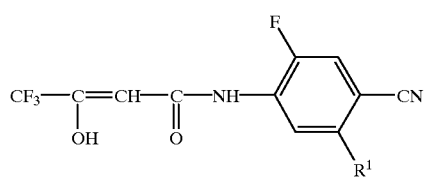

(Ib)

For simplicity's sake, only the "keto" form is given in each case.

The trifluoroacetoacet-anilides of the formula (I) preparable according to the invention are useful intermediates for the synthesis of uracil derivatives having herbicidal properties.

Thus, uracil derivatives of the formula

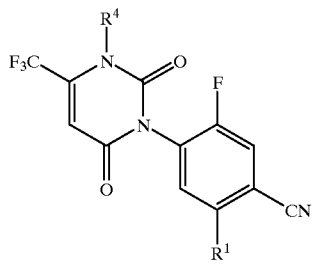

(IV)

in which
$R^1$ is as defined above and
$R^4$ represents hydrogen, hydroxyl, amino, represents methyl, ethyl, n- or i-propyl, n-, i-, s- or t-butyl, methoxy, ethoxy, n- or i-propoxy, n-, i-, s- or t-butoxy, each of which is optionally substituted by hydroxyl, cyano, fluorine, chlorine, methoxy or ethoxy, or represents propenyl, butenyl, propinyl or butinyl, each of which is optionally substituted by cyano, fluorine, chlorine or bromine
can be prepared by reacting trifluoroacetoacet-anilides of the formula

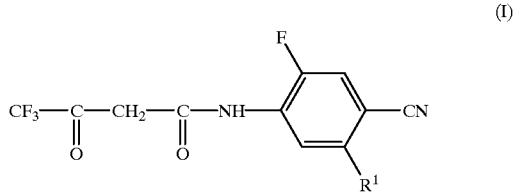

(I)

in which
$R^1$ is as defined above,
with phosgene in the presence of an acid binder, such as pyridine or 4-dimethylaminopyridine, and in the presence of a diluent, such as toluene or tetrahydrofuran, at temperatures between −20° C. and +150° C., and reacting the resulting phenyloxazine-diones of the formula

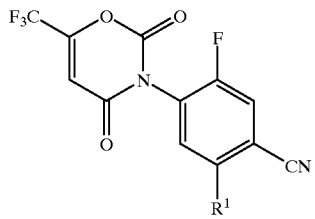

(V)

in which
$R^1$ is as defined above,
with amino compounds of the formula $H_2N—R^4$ (VI)

in which
$R^4$ is as defined above,
if appropriate in the presence of an acid binder and if appropriate in the presence of a diluent, such as ethanol, at temperatures between −50° C. and +80° C.

The uracil derivatives of the formula (IV) and their use as herbicides are known (cf. EP-A 0 408 382, EP-A 0 648 749 and WO 95–32 952).

The process according to the invention is illustrated by the examples which follow.

PREPARATION EXAMPLES

Example 1

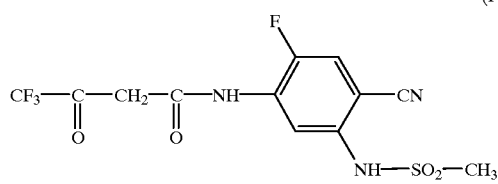
(I-1)

Under an atmosphere of argon and at 20 to 22° C., 40.4 g of a 35% strength solution of trifluoroacetoacetyl chloride (81 mmol) in methylene chloride are added dropwise with stirring over a period of 15 minutes to a suspension of 10.3 g (45 mmol) of 4-cyano-2-fluoro-5-methylsulphonylamino-aniline and 4.28 g (54 mmol) of pyridine in 110 ml of methylene chloride. After the addition, the dropping funnel is rinsed with 10 ml of methylene chloride which are also added dropwise to the reaction mixture. The progress of the reaction is monitored by thin-layer chromatography. After a reaction time of 15 minutes, the mixture is worked up by cooling to 0° C., filtering off the resulting precipitate, rinsing with methylene chloride and drying. This gives 15 g of a pulverulent substance which is admixed with water. The resulting mixture is extracted three times with ethyl acetate. The combined organic phases are, after drying over sodium sulphate, concentrated under reduced pressure. The product that remains is dried under reduced pressure. This gives 12.2 g (73.8% of theory) of N-(4-cyano-2-fluoro-5-methylsulphonylamino-phenyl)-4,4,4-trifluoro-3-oxo-butyramide in the form of a solid substance of melting point 186 to 191° C.

Example 2

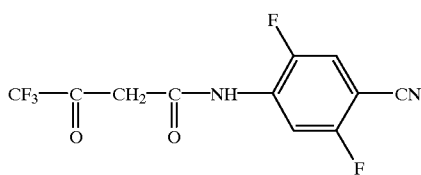
(I-2)

Under an atmosphere of argon and with stirring, 713 g of a solution of trifluoroacetoacetyl chloride (1.43 mol, 35% strength solution) in methylene chloride are added dropwise over a period of 25 minutes to a mixture of 169.5 g (1.1 mol) of 2,5-difluoro-4-cyano-aniline, 104.5 g of pyridine (1.32 mol) and 640 ml of methylene chloride cooled to 10° C. After the addition, the dropping funnel is rinsed with 20 ml of methylene chloride which are also added dropwise to the reaction mixture. The progress of the reaction is monitored by thin-layer chromatography. the reaction mixture is stirred at 22° C. for 1 hour and then cooled to 0° C. and stirred at this temperature for 15 minutes. The precipitate is filtered off, washed with methylene chloride and dried. This gives 209.3 g of a crude product which is admixed with water. The resulting mixture is repeatedly extracted with ethyl acetate. The aqueous phase is made strongly acidic using concen-
trated hydrochloric acid and once more extracted with ethyl acetate. The combined organic phases are washed with water and then dried over sodium sulphate. The solution which remains after the filtration is concentrated under reduced pressure. The product that remains is dried under reduced pressure. This gives 150.4 g (47.1% of theory) of N-(4-cyano-2,5-difluoro-phenyl)-4,4,4-trifluoro-3-oxo-butyramide in the form of a white solid of melting point 176 to 181° C.

By repeat work-up of the mother liquor in the abovementioned manner, further product in the form of the hydrate of the compound of the formula (I-2) is isolated. The total yield is 54% of the theory.

Example 3

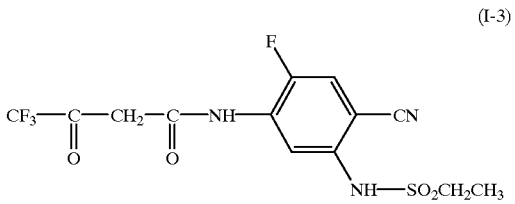
(I-3)

By the method of Example 1, 4-cyano-2-fluoro-5-ethylsulphonylamino-aniline gives N-(4-cyano-2-fluoro-5-ethylsulphonylamino-phenyl)-4,4,4-trifluoro-3-oxobutyramide of melting point from 185 to 187° C.

Use Example A

Preparation of the compound of the formula

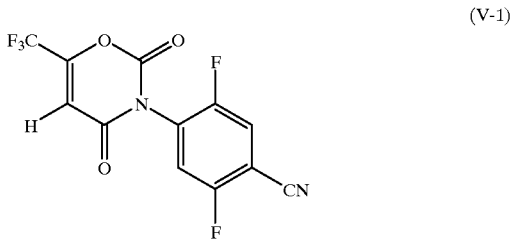
(V-1)

At 40° C., 120 g of a 20% strength solution of phosgene in toluene are added dropwise with stirring to a mixture of 60 g (0.20 mol) of N-(4-cyano-2,5-difluoro-phenyl)-3-oxo-4,4,4-trifluoro- 1-butyramide, 40 ml of pyridine, 4 g of 4-dimethylamino-pyridine and 1.5 liters of toluene. The reaction mixture is then stirred at 40° C. for another 4 hours. Excess phosgene is subsequently flushed out with nitrogen. The mixture that remains is washed three times with water, dried over sodium sulphate and filtered. The solvent is carefully distilled off from the filtrate under waterpump vacuum.

This gives 63.7 g (77.5% of theory) of 3-(4-cyano-2,5-difluoro-phenyl)-3,4-dihydro-6-trifluoromethyl-2H- 1,3-oxazine-2,4-dione as a viscous material which slowly crystallizes.

Preparation of the compound of the formula

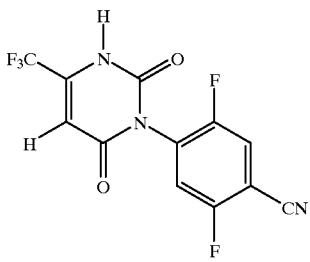
(IV-1)

At room temperature (approximately 20° C.), 7 ml of a 25% strength aqueous solution of ammonia (0.10 mol of NH₃) are added dropwise with stirring to a mixture of 15.9 g (0.05 mol) of 3-(4-cyano-2,5-difluoro-phenyl)-3,4-dihydro-6-trifluoromethyl-2H- 1,3-oxazine-2,4-dione and 100 ml of ethanol. The reaction mixture is stirred at room temperature for 20 hours. The mixture is then concentrated under waterpump vacuum and the residue is taken up in ethyl acetate. The resulting solution is washed with water, dried over sodium sulphate and filtered. The filtrate is concentrated under reduced pressure, the residue is digested with a little isopropanol and the resulting crystalline product is isolated by filtration with suction.

This gives 11.8 g (74% of theory) of 1-(4-cyano-2,5-difluoro-phenyl)-3,6-dihydro-2,6-dioxo-4-trifluoromethyl-1 (2H)-pyrimidine of melting point 234° C.

What is claimed is:

1. Process for preparing trifluoroacetoacet-anilides of the formula

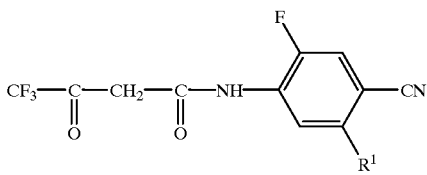
(I)

in which
R¹ represents halogen or a radical of the formula

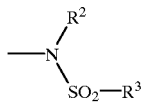

in which
R² represents hydrogen or optionally substituted alkyl and
R³ represents optionally substituted alkyl, optionally substituted cycloalkyl or represents optionally substituted aryl,
characterized in that trifluoroacetoacetyl chloride of the formula

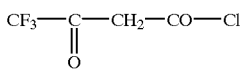
(II)

is reacted with anilines of the formula

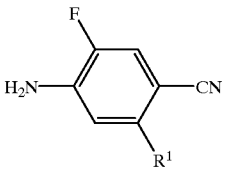
(III)

in which
R¹ is as defined above,
if appropriate in the presence of an acid binder and if appropriate in the presence of a diluent, at temperatures between −20° C. and +40° C.

2. Process according to claim 1, characterized in that the starting materials used are anilines of the formula (III) in which
R¹ represents fluorine, chlorine, bromine or a radical of the formula

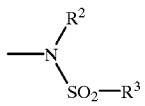

in which
R² represents hydrogen or represents alkyl having 1 to 6 carbon atoms which is optionally substituted by cyano, halogen, alkoxy having 1 to 4 carbon atoms, alkylthio having 1 to 4 carbon atoms, alkylcarbonyl having 1 to 4 carbon atoms in the alkyl group or alkylaminocarbonyl having 1 to 4 carbon atoms in the alkyl moiety and
R³ represents alkyl having 1 to 6 carbon atoms, which is optionally substituted by cyano, halogen, $C_1$–$C_4$-alkoxy, $C_1$–$C_4$-alkylthio, $C_1$–$C_4$-alkylcarbonyl, $C_1$–$C_4$-alkoxycarbonyl, $C_1$–$C_4$-alkylaminocarbonyl or phenyl,
or represents cycloalkyl having 3 to 6 carbon atoms which is optionally mono- to trisubstituted by identical or different substituents selected from the group consisting of halogen, cyano and alkyl having 1 to 4 carbon atoms, or represents
phenyl which is optionally mono- to trisubstituted by identical or different substituents selected from the group consisting of halogen, cyano, alkyl having 1 to 4 carbon atoms, halogenoalkyl having 1 or 2 carbon atoms and 1 to 5 halogen atoms, alkoxy having 1 to 4 carbon atoms and halogenoalkoxy having 1 or 2 carbon atoms and 1 to 5 halogen atoms.

3. Process according to claim 1, characterized in that the starting materials used are anilines of the formula (III) in which
R¹ represents fluorine, chlorine or a radical of the formula

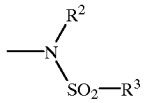

in which
R² represents hydrogen or represents methyl, ethyl, n- or i-propyl, n-, i-, s- or t-butyl, each of which is optionally substituted by cyano, fluorine, chlorine, methoxy, ethoxy, methylthio, ethylthio, acetyl, propionyl, methoxycarbonyl, ethoxycarbonyl, methylaminocarbonyl or ethylaminocarbonyl and $R^3$ represents methyl, ethyl, n- or i-propyl, n-, i-, s- or t-butyl, each of which is optionally substituted by cyano, fluorine, chlorine, methoxy, ethoxy, methylthio, ethylthio, acetyl, propionyl, methoxycarbonyl, ethoxycarbonyl, methylaminocarbonyl, ethylaminocarbonyl or phenyl or represents cyclopentyl, cyclohexyl or cyclopropyl, which is optionally mono- to trisubstituted by identical or different substituents selected from the group consisting of fluorine, chlorine, cyano, methyl and ethyl, or represents phenyl which is optionally mono- to trisubstituted by identical or different substituents selected from the group consisting of fluorine, chlorine, cyano, methyl, ethyl, trifluoromethyl, methoxy, ethoxy, trifluoromethoxy and difluoromethoxy.

4. Process according to claim 1, characterized in that the starting material used is the aniline of the formula

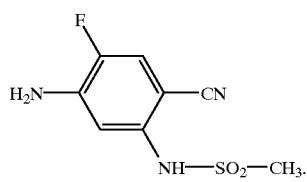

5. Process according to claim 1, characterized in that the starting material used is the aniline of the formula

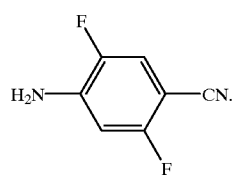

6. Process according to claim 1, characterized in that the starting material used of the aniline of the formula

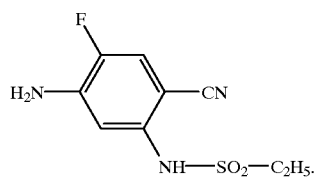

7. Process for preparing uracil derivatives of the formula (IV)

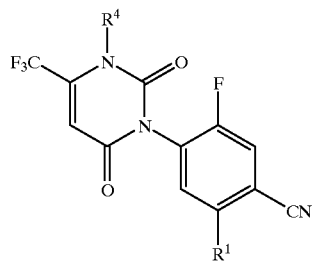

in which $R^1$ is

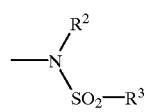

in which $R^2$ represents hydrogen or optionally substituted alkyl and $R^3$ represents optionally substituted alkyl, optionally substituted cycloalkyl, or optionally substituted aryl, and $R^4$ represents hydrogen, hydroxyl, amino, represents methyl, ethyl, n- or i-propyl, n-, i-, s- or t-butyl, methoxy, ethoxy, n- or i-propoxy, n, i-, s- or t-butoxy, each of which is optionally substituted by hydroxyl, cyano, fluorine, chlorine, methoxy or ethoxy, or represents propenyl, butenyl, propinyl or butinyl, each of which is optionally substituted by cyano, fluorine, chlorine or bromine, characterized in that trifluoroacetoacet-anilides of the formula (I)

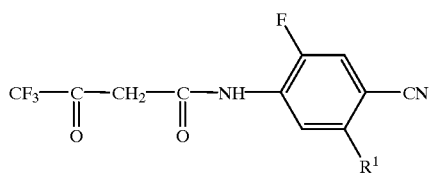

in which $R^1$ is as defined above, are reacted with phosgene in the presence of an acid binder and in the presence of a diluent at temperatures between −20° C. and +150° C., and the resulting phenyloxazine-diones of the formula

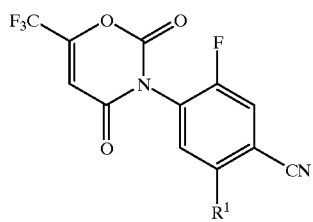
in which
R¹ is as defined above
are reacted with amino compounds of the formula
$$H_2N-R^4 \quad (VI)$$
in which
R⁴ is as defined above,
if appropriate in the presence of an acid binder and if appropriate in the presence of a diluent, at temperatures between −50° C. and +80° C.
* * * * *